(12) United States Patent
Burke et al.

(10) Patent No.: US 8,163,241 B2
(45) Date of Patent: Apr. 24, 2012

(54) OPTICAL PROBE

(75) Inventors: Conor Stephen Burke, Dublin (IE);
Thomas Ruckstuhl, Zurich (CH); John Moore, Dublin (IE)

(73) Assignee: Dublin City University DCU, Dublin (IE)

( * ) Notice: Subject to any disclaimer, the term of this patent is extended or adjusted under 35 U.S.C. 154(b) by 333 days.

(21) Appl. No.: 12/299,666

(22) PCT Filed: May 7, 2007

(86) PCT No.: PCT/IB2007/003920
§ 371 (c)(1),
(2), (4) Date: Dec. 16, 2008

(87) PCT Pub. No.: WO2008/029298
PCT Pub. Date: Mar. 13, 2008

(65) Prior Publication Data
US 2009/0191092 A1 Jul. 30, 2009

Related U.S. Application Data

(60) Provisional application No. 60/798,423, filed on May 5, 2006.

(51) Int. Cl.
*G01N 21/00* (2006.01)
*G01N 21/76* (2006.01)
*G01J 3/30* (2006.01)
*G01N 21/64* (2006.01)
*G01N 27/26* (2006.01)
*G01N 21/75* (2006.01)

(52) U.S. Cl. ............ 422/82.11; 422/52; 422/82.05; 422/82.07; 422/82.08; 422/400; 356/317; 204/400

(58) Field of Classification Search .............. None
See application file for complete search history.

(56) References Cited

U.S. PATENT DOCUMENTS

| 3,838,277 | A  | * | 9/1974 | Morgenstern et al. | 250/216 |
| 5,080,865 | A  | * | 1/1992 | Leiner et al. | 422/68.1 |
| 7,289,204 | B2 | * | 10/2007 | Nielsen et al. | 356/317 |
| 7,416,703 | B2 | * | 8/2008 | Murray et al. | 422/91 |

(Continued)

FOREIGN PATENT DOCUMENTS

WO  WO 02/090948  11/2002

OTHER PUBLICATIONS

Ruckstuhl et al., "Highly Sensitive biosensing using a supercritical angle fluorescence instrument," Biosensors and Bioelectronics, vol. 18, Aug. 15, 2003, pp. 1193-1199.*
Authors: Thomas Ruckstuhl, Michael Rankl, Stefan Seeger; Title: Highly Sensitive Biosensing Using a Supercritical Angle Flourescence Instrument; Biosensors and Bioelectronics, vol. 18, Aug. 15, 2003, pp. 1193-1199, XP002475568 paragraphs [0001], [0002].

*Primary Examiner* — In Suk Bullock
*Assistant Examiner* — Jennifer Wecker
(74) *Attorney, Agent, or Firm* — Brown Rudnick LLP; Mark Leonardo (57) ABSTRACT

An optical probe for detecting luminescence emitted by a sample is disclosed. The optical probe includes a parabolic optical waveguide and an outer housing having a detachable component configured to hold a transparent sensor substrate that can be coupled to the optical waveguide. The optical probe also includes a sensing material for detection of at least one specified analyte. An excitation source is configured to excite the sensing material. The optical probe also incorporates a measuring photodetector that detects emitted luminescence.

11 Claims, 7 Drawing Sheets

U.S. PATENT DOCUMENTS

2002/0098120 A1* 7/2002 Blazewicz et al. ......... 422/82.07
2002/0151772 A1* 10/2002 Polak ........................... 600/310
2004/0256560 A1* 12/2004 Russell ....................... 250/338.5
2006/0228260 A1* 10/2006 Nishiuma .................. 422/82.11

* cited by examiner

OPTICAL PROBE

RELATED APPLICATION INFORMATION

This patent application claims priority to U.S. Provisional Application No. 60/798,423 filed in the U.S. on May 5, 2006.

BACKGROUND

1. Technical Field

The present disclosure generally relates to the Held of optical sensor probes for collection of luminescence generated at a dielectric interface, and more particularly, an optical sensor probe employing a parabolic optical waveguide optimized for the efficient collection of luminescence generated at a dielectric interface.

2. Description of the Related Art

Optical sensors are widely used across a broad range of industrial applications in industries including, for example, biomedical, environmental and food packaging. Luminescence-based optical sensors detect analyte-induced changes in a luminescence signal. Such changes may be brought about due to the analyte-induced quenching of luminescence from an analyte-sensitive luminescent compound, which is the case for a broad range of optical chemical sensors including sensors for oxygen, carbon dioxide, pH and chloride. In such cases, the luminescent compound is typically encapsulated within a porous, solid matrix that can be deposited onto a substrate as a thin film. Alternatively, luminescence-based optical sensors may be based on the binding of the analyte of interest to a surface using suitable receptor molecules. Luminescence is imparted to such a system through the use of a luminescent label that can be attached to the analyte itself or to an additional molecule that binds to the surface-bound analyte. Changes in the level of luminescence are indicative of changes in the concentration of analyte that is bound to the surface. This methodology is commonly employed for the development of luminescence-based optical biosensors.

In order to sensitively measure the concentration of analyte molecules bound to the receptor molecules, it is necessary to detect only the luminescence that originates from surface-bound molecules. From this, it follows that the measurement task is to detect selectively luminescence from molecules bound close to the surface, excluding any signal from unbound molecules in the environment above the surface. This detection principle, is also relevant to thin film-based optical chemical sensors.

An understanding of the nature of luminescence emission at a dielectric surface is necessary in order to efficiently detect luminescence and develop effective optical chemical/biological sensors. The anisotropic nature of this emission has prompted the development of novel optical configurations designed to more efficiently capture luminescence that has been generated at or near a dielectric surface, for example, U.S. Pat. No. 6,714,297 to Seeger and Ruekstuhl, which is hereby incorporated herein by reference. That reference describes the detection of supercritical angle fluorescence (SAF), which is generated by luminescent molecules located at or near a dielectric surface by using a parabolic optical waveguide. This detection ability improves the amount of fluorescence that can be detected in addition to being a surface-selective detection mechanism.

Unfortunately, current optical arrangements are costly and it is often difficult to change optical components in the event that the user would like to monitor a variety of analytes. Additionally, many of these optical arrangements have low efficiency due to the fact that their ability to collect emitted luminescence is limited.

Therefore, it would be desirable to provide a robust, low-cost, portable optical sensor probe that is capable of the efficient detection of luminescence for the development of highly-sensitive sensors. The sensor probe should incorporate an apparatus that allows for the efficient collection of surface-generated luminescence and the detection principle can be intensity-based or lifetime-based depending on the desired application. The probe should also be modular in nature, facilitating the detection of a variety of analytes using the correct combination of sensing material and optical/optoelectronic components.

SUMMARY

Accordingly, an optical probe for detecting luminescence emitted by a sample is disclosed. The optical probe includes a parabolic optical waveguide and an outer housing configured to hold the optical waveguide having a detachable component. The optical probe also includes a sensing material for detection of at least one analyte. An excitation source is configured to excite the sensing material and a measuring photodetector detects emitted luminescence. In another embodiment, the optical probe further includes a waveguide mount between the outer housing and the detachable component configured to hold the waveguide in place, collection optics to focus emitted light onto the photodetector and an emission filter configured to allow emitted light to pass.

In another embodiment, the optical probe includes a transparent sensor substrate, such as, for example, a cover slip or microscope slide, between the detachable component and the waveguide. The sensing material may be deposited on the transparent sensor substrate. In an alternative embodiment, the sensing material may be deposited directly on the waveguide.

In yet another embodiment, the optical probe includes an airway adapter attached to the optical probe. The airway adapter allows for foe detection of a user's breath.

The optical probe may be used to detect various analytes including, but not limited to, oxygen, carbon dioxide, pH, phosphate, nitrate, ammonia, chloride, other chemical species or a range of biomolecules such as DNA, enzymes or antibodies.

In another embodiment, the optical probe includes a reference photodiode configured to measure backscatter from said excitation source. Also, at least one sealing ring may be incorporated to provide connection between the outer housing, the waveguide mount, the waveguide, and the detachable component.

In yet another embodiment, the optical probe includes a measuring photomultiplier tube.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings as set forth below:

DETAILED DESCRIPTION OF EXEMPLARY EMBODIMENTS

Figure 1:
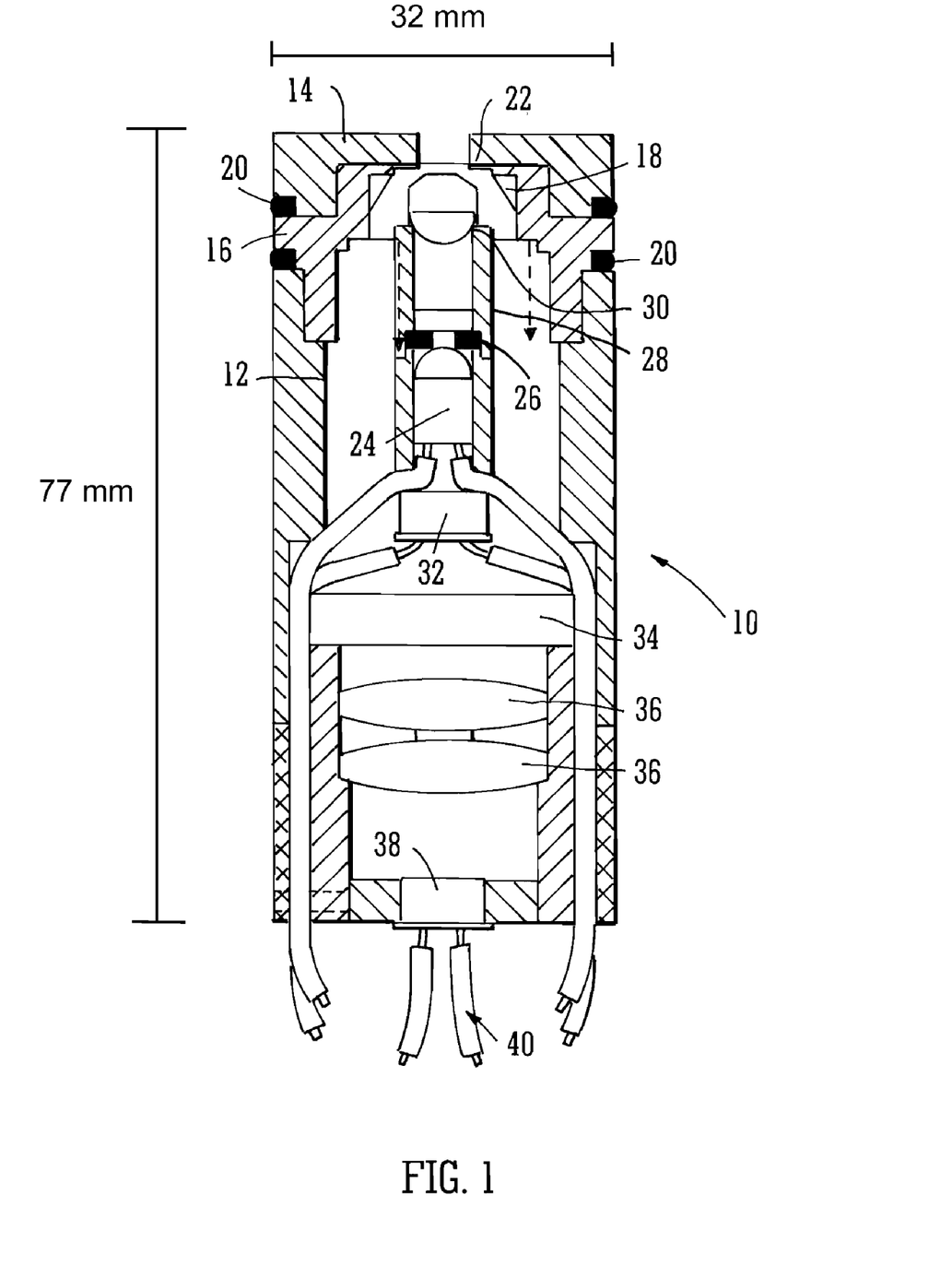
FIG. 1 is a plan cross-sectional view of one embodiment of an optical sensor probe, in accordance with the principles of the present disclosure.

The various exemplary embodiments of the present invention are directed to optical sensor probes that include a parabolic optical waveguide, optimized for the efficient collection of fluorescence generated at a dielectric interface. An optimized optical configuration and probe of the current disclosure is shown in FIG. 1 and incorporates a waveguide with low cost components arranged in a probe geometry. FIG. 1 shows an optical sensor probe configuration that may be used for gas and/or chemical sensing applications. Additionally, the optical sensor probe configuration may be used in biosensing applications. The apparatus may be used for luminescence intensity-based or lifetime-based measurements. The dimensions shown are merely indicative of the scale of the device itself. The size of the probe can be tailored to suit specific applications.

More specifically, an optical sensor probe 10 includes an outer housing 12 with a detachable cap 14, between which is a waveguide mount 16 fixing in place a parabolic optical waveguide 18. The detachable cap may be any removable or replaceable component that assists in placement and application of a sensing material. The connections between the outer housing 12 and waveguide mount 16, and the detachable cap 14 and waveguide mount 16 are optional sealing rings 20, which may be employed if required by the application. Between the cap 14 and the waveguide 18 is a transparent sensor substrate 22 upon which the sensing material may be deposited. Tire transparent sensor substrate 22 may be, for example, a cover slip or a microscope slide. Additionally, an immersion oil may be used to ensure good optical transmission between the waveguide 18 and the transparent sensor substrate 22. In an alternative embodiment, the sensing material may be deposited directly onto the waveguide 18. The detachable cap 14 is used to house the transparent sensor substrate 22 onto which the sensing material is deposited. In the current embodiment, the sensor substrate is attached to the cap by means of an adhesive and the cap is threaded for ease of connection to the waveguide mount 16. If it is desired to change the sensing functionality of the probe, this can be achieved by attaching a sensor cap that houses a sensor substrate onto which a different sensing material has been deposited. However, it is envisioned that in other embodiments of the probe, the sensing cap could have an integrated sensing region that replaces the sensor substrate, making the cap itself a disposable sensing element.

The parabolic optical waveguide may be constructed of plastic or glass. However, other materials and media may be used including a liquid medium surrounding the waveguide or other solid bodies such as a plastic/glass interface.

The sensing material is excited using an excitation source 24. The excitation source 24 may be, for example, an excitation LED such that fluorescent light is emitted when the excitation LED excites the sensing material. The light from the excitation source 24 passes through an aperture 26 and an excitation filter 28 before being focused by a lens 30 on the sensing material. The excitation filter 28 removes from the excitation light any spectral components that may coincide with the transmission region of the emission filter 34, components that would otherwise lead to an undesirably high background signal.

A reference photodiode 32 may be used to measure backscatter from the excitation source, thereby providing compensation for fluctuations in the emission of the source.

Figure 2:
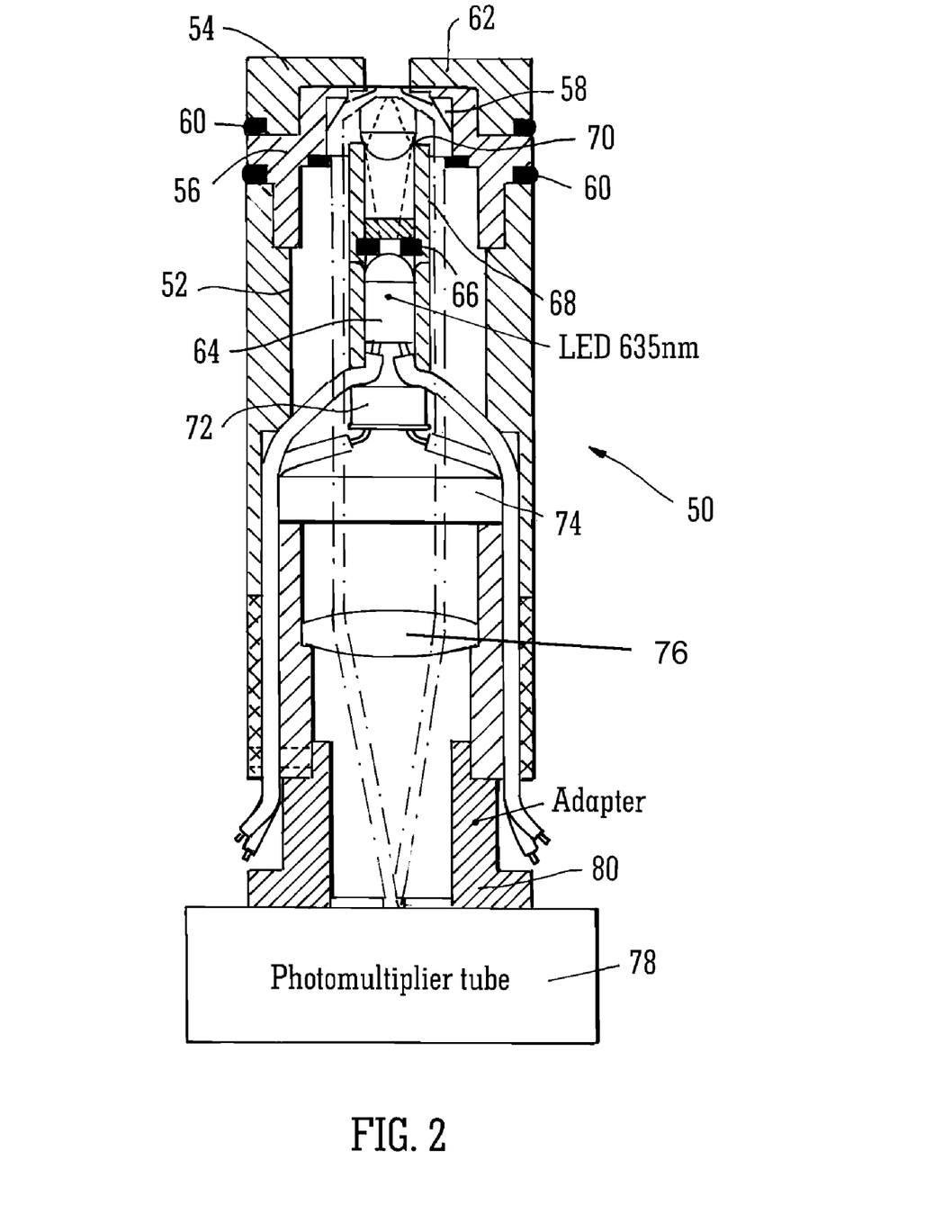
FIG. 2 is a plan cross-sectional view of another embodiment of an optical sensor probe, in accordance with the principles of the present disclosure.

The sensing material will emit luminescence in the presence of the molecule of interest. The sensing material should be selected so that its absorption wavelength coincides with the emission wavelength of the light source. For example, ruthenium or porphyrin complexes, Rhodamine or a Cyanin dye such as Cy5 may be suitable fluorescent dyes. The parabolic optical waveguide 18 is configured such that luminescence emitted from the sensing material is directed towards the detection set up. As will be discussed in further detail below, FIG. 2 shows the emitted ray path. Referring back to FIG. 1, the emitted light passes through an emission filter 34 and collection optics 36 before being detected by a measuring photodetector 38.

The measuring photodetector 38 may be, for example, an avalanche photodiode suitable for counting single photons, a silicon PIN photodiode, a photomultiper, or a CCD chip. Also shown is wiring 40 which is used to control the various elements described herein. The signal output from the measuring photodetector 38 is acquired and processed using appropriate software.

The optical probe 10 may include, for example, LED (Roithner LaserTechnik, 450-06U; max=450 nm), excitation filter (Semrock, FF01-447-60), emission filter (Semrock, FF01-583-120), focusing lens (Edmund Optics, 6 mm halfball, NT45-935), photodiodes (Hamamatsu, S1223-01, Si PIN photodiode) and collection optics (Edmund Optics, double convex lens (×2), NT45-294).

An optical probe according to the present disclosure is shown in FIG. 2. FIG. 2 shows an optical probe 50 that is configured for biosensing applications and is tailored for the detection of Cy5, Cyanin fluorescence. The optical probe 50 of FIG. 2 includes an outer housing 52 with a detachable cap 54, between which is a waveguide mount 56 fixing in place a waveguide 58. The connections between the outer housing 52 and waveguide mount 56, and the detachable cap 54 and waveguide mount 56 are optional sealing rings 60. A transparent sensor substrate 62 is between the cap 54 and the waveguide 58. Sensing material may be deposited on the transparent sensor substrate 62 or may also be deposited directly onto the waveguide 58.

The sensing material is excited using an excitation source 64. The light from the excitation source 64 passes through an aperture 66 and an excitation filter 68 before being focused by a lens 70 on the sensing material. A reference photodiode 72 may be used to measure backscatter from the excitation source. The emitted light from the sensing material passes through an emission filter 74 and collection optics 76 before being detected by a measuring photomultiplier tube (PMT) 78.

Also, included in the optical sensor probe shown in FIG. 2 is a super critical angle fluorescence aperture (SAF aperture)

to block signals that are not generated by surface-specific binding. The adapter 80 acts a physical interface between the optical probe and the PMT, allowing the user to "plug" the PMT into the output of the probe.

The optical probe as shown in FIGS. 1 and 2 may be used for the detection, of a variety of analytes and/or parameters. A broad range of gases or chemicals may be detected, given a suitable, fluorescence-based sensing chemistry. For example, oxygen, carbon dioxide, pH, phosphate, nitrate, chloride, ammonia or other chemicals of interest can be detected. The probe may also be used as an optical biosensor for the detection of biomolecules such as, but not limited to, DNA, enzymes or antibodies.

Figure 3:
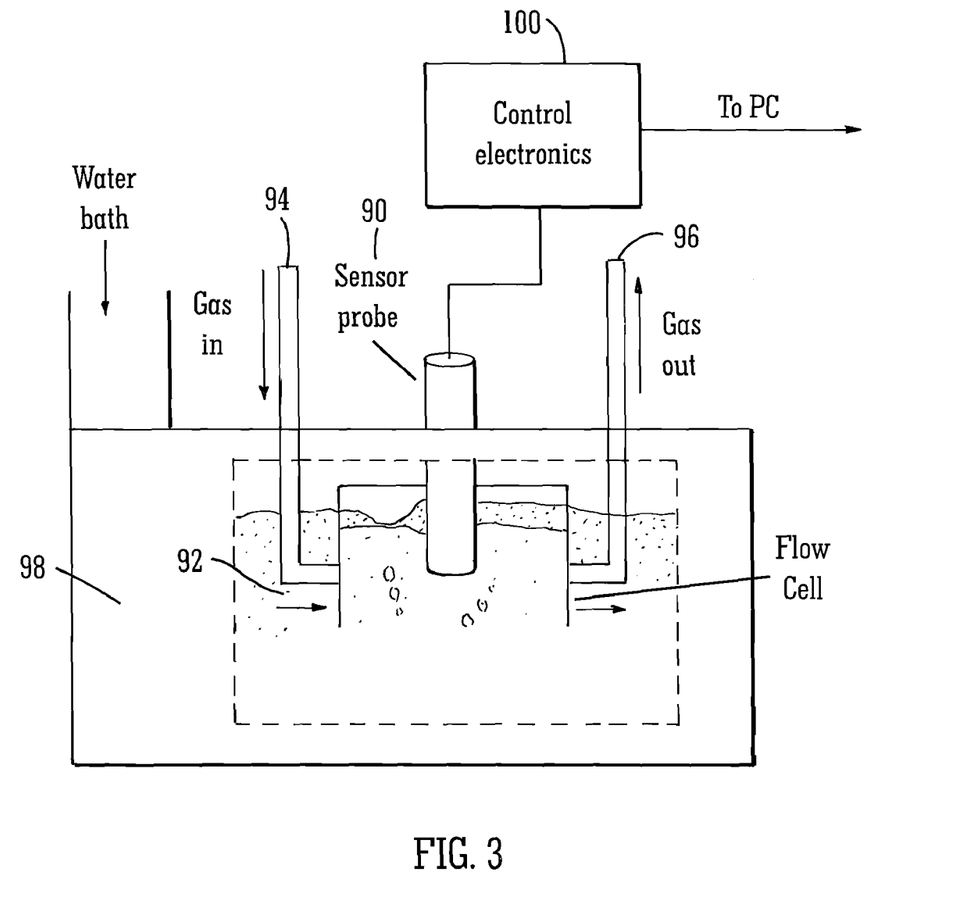
FIG. 3 is a schematic view of one use of the optical sensor probe shown in FIG. 1.

By way of non-limiting example, an optical probe 90 was integrated into a durable polymer housing and subsequently applied to the detection of dissolved oxygen (DO) as a proof of principle, employing phase fluorometric detection as shown in FIG. 3. The probe 90 was immersed in a flow cell 92 of de-ionised water with integrated gas flow connections. Gas entered at a gas inlet 94 and the gas exited at a gas outlet 96. Varying oxygen concentrations were bubbled through using MFC's (mass flow controllers). The flow cell 92 was submerged in a water bath 98, which maintained a constant working temperature of 20° C. for the duration of the experiment. Control electronics 100 were used to control the experiment. The signal was acquired and processed using a custom-written Lab VIEW VI (National Instruments™ UK).

The sensing material was a known sol-gel thin film based on a n propyltriethoxysilane (PTEOS) precursor containing the fluorescent ruthenium complex [Ru(II)-tris(4,7-diphenyl-1,10-phenanthroline)] $(Ru(dpp)_3^{2+})$. The film preparation may include 1 mole PTEOS/4 H2O/6.25 EtOH/7.2×10-3 HCl with a molar ratio dye $[Ru(dpp)_3^{2+}]$/PTEOS=1.4×10-3; dissolve $[Ru(dpp)_3^{2+}]$ in EtOH and stir until complex dissolves; add PTEOS while stirring; and add HCl (pH 1) slowly, dropwise while stirring. The solution may be left stirring for at least 3 weeks before use.

Figure 4:
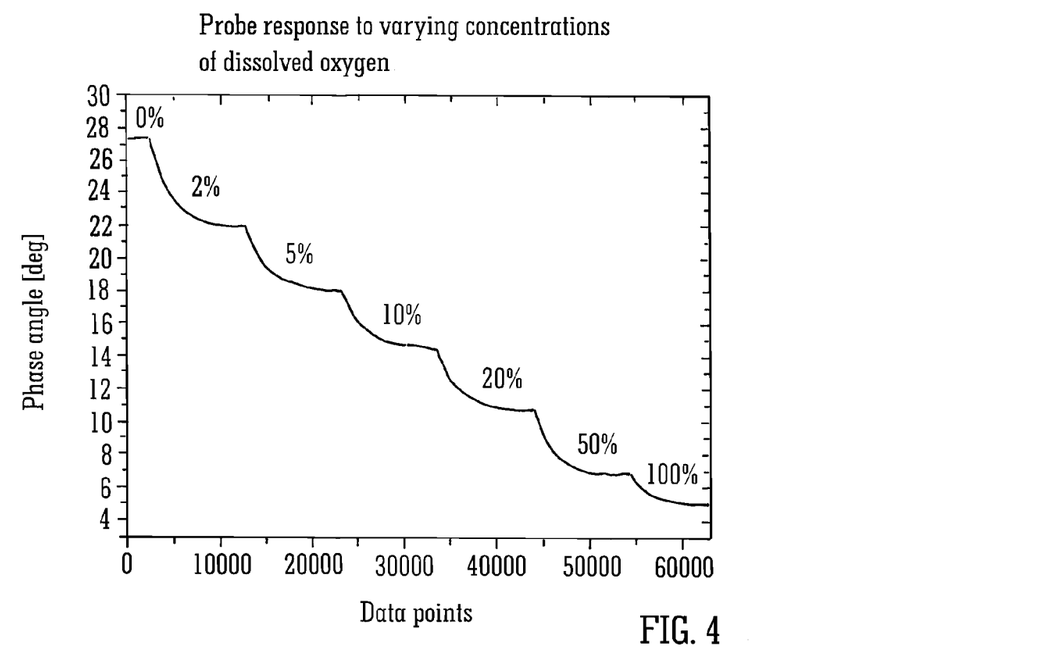
FIG. 4 is a chart showing the response of the optical sensor probe of FIG. 1 as a (unction of dissolved oxygen concentration.
Figure 5:
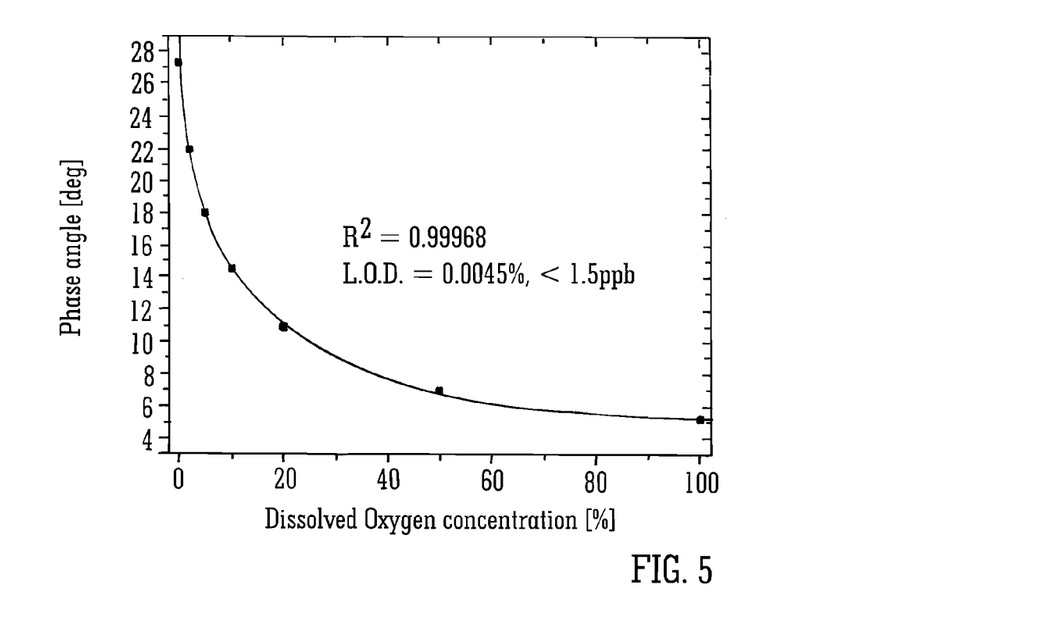
FIG. 5 is a chart showing a corresponding calibration curve of FIG. 4.

The probe response as a function of dissolved oxygen (DO) concentration is shown in FIG. 4 with the corresponding calibration curve shown in FIG. 5. The limit of detection (LOD) for DO was determined to be less than 1.5 ppb, with an integration time of 0.6 seconds. The LOD compares favorably to an electrochemical dissolved oxygen sensor available commercially from YSI (e.g., YSI product—product name YSI 550A Dissolved Oxygen Meter—Minimum resolution 0.01 mg/L or 10 ppb).

Figure 6:
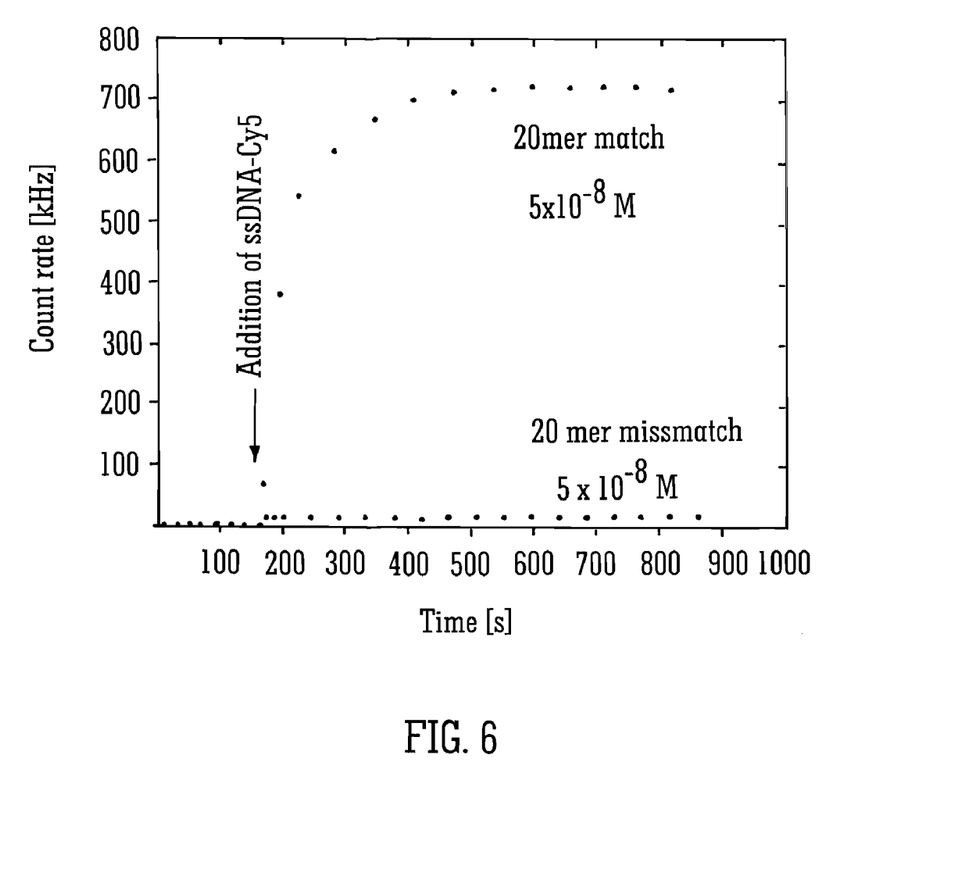
FIG. 6. is a chart showing real-time detection of DNA hybridization.

According to the present disclosure, a graph representing real-time detection of DNA hybridization is shown in FIG. 6. FIG. 6 shows two curves that were recorded by a photon-counting photomultiplier tube (PMT) to which the probe was attached, as shown in FIG. 2. The luminescence signal increases significantly for one curve and remains relatively unchanged for the other. The former represents the response of the sensor to a 20-mer match sample of single stranded DNA, which was labeled with the fluorescent indicator, Cy5. Each data point corresponds to the number of photons recorded by the PMT over a period of 500 ms. The marked increase in signal upon introduction of the 20-mer match sample is indicative of binding of the sample DNA to the receptor DNA on the surface of the sensor sample. The second curve indicates that no binding is occurring at the surface, which was expected for the case of the mismatched sample. These data illustrate the ability of the optical probe to provide real-time measurement of surface binding events for biosensing applications.

Figure 7:
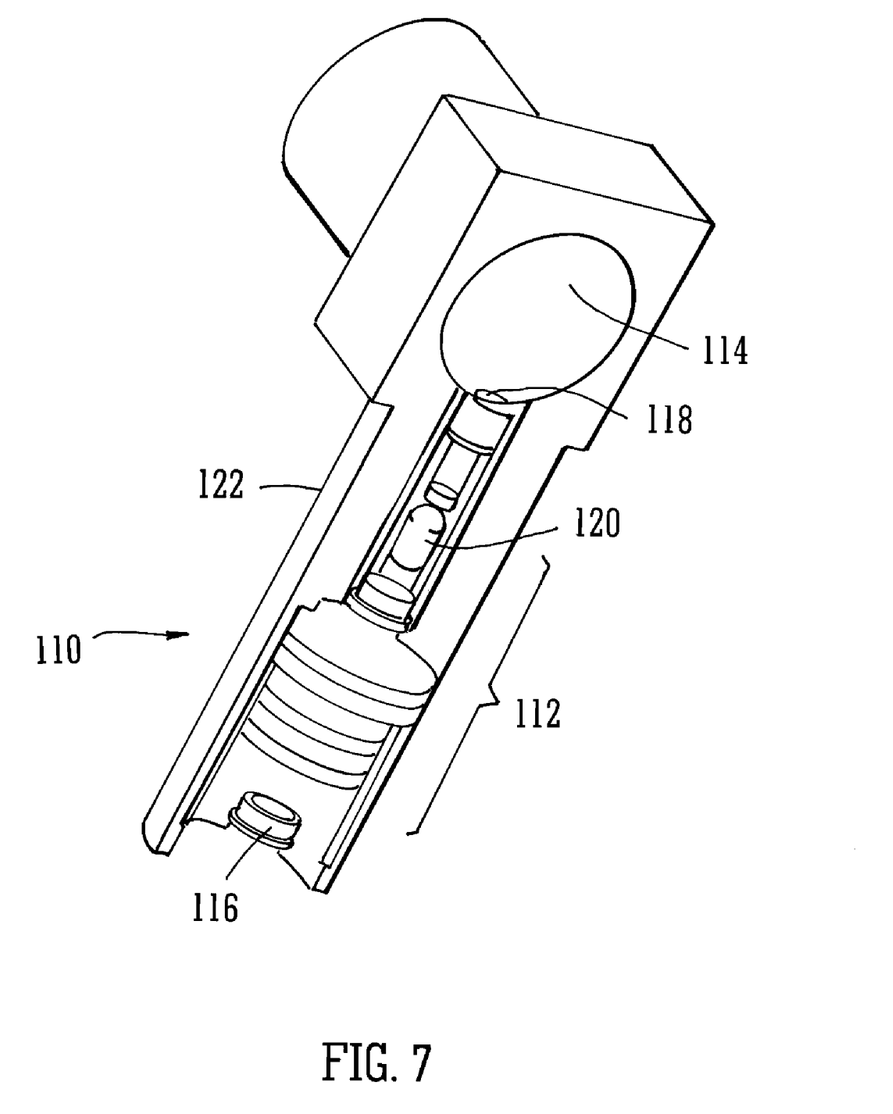
FIG. 7 is a schematic view of the use of the optical sensor probe according to the present disclosure incorporated in a breath monitoring device.

A hand-held device for breath gas analysis 110 is shown in FIG. 7. An airway adapter 114 is connected to the optical probe 112. For this application, the airway adapter replaces the detachable sensor cap 14 shown in FIG. 3. The probe 120 may be surrounded by housing 122. The airway adapter 114 allows a user's breath to interact with the sensing element 118 of the optical sensing probe 120. The hand-held device 110 may be configured to be connected to a power source, a PC, a PDA or other device to assist in the gathering and processing of information. It is also contemplated that the probe according to the present disclosure may be incorporated into a mask to monitor a user's breath. The device may also be wireless to provide ease of mobility for the user.

Figure 8:
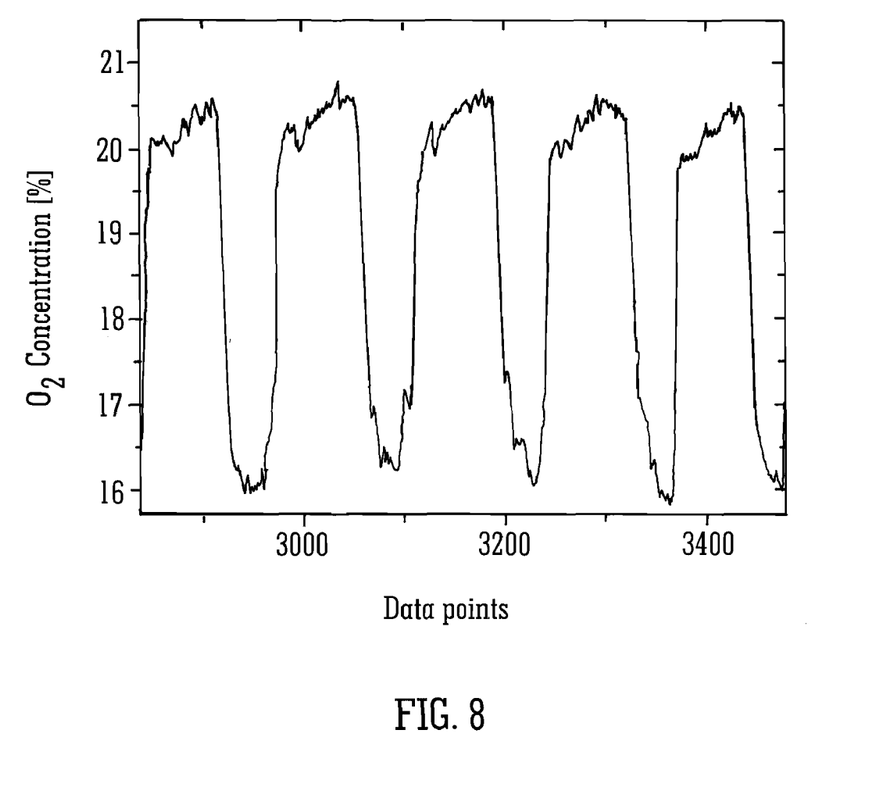
FIG. 8 is a chart showing real time detection of oxygen during breath monitoring.

FIG. 8 shows real-time detection of oxygen in human breath. The data were recorded by having a test subject breathe into the airway adapter 114 while at rest, which corresponds to a breath rate of approximately 10 breaths per minute. An oxygen-sensitive sol-gel material, as previously described, was deposited onto the sensing element and the fluorescence from this material was recorded in real-time while the test subject breathed through the airway adapter 114. FIG. 8 shows the real-time evolution of the in-breath oxygen concentration as recorded by the sensor. The system is compatible with the detection of a broad range of analytes in breath, including carbon dioxide, ammonia and anaesthetic gases, given a suitable sensing material.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An optical probe for detecting luminescence emitted by a sample comprising:
    a parabolic optical waveguide;
    an outer housing configured to hold said optical waveguide having a detachable component;
    a waveguide mount between said outer housing and said detachable component configured to hold said waveguide in place;
    a sensing material for detection of at least one analyte;
    an excitation source comprising an LED configured to pass light through a half-ball focusing lens which focuses light onto said sensing material to excite said sensing material;
    an emission filter configured to allow emitted light to pass;
    collection optics to focus emitted light onto a photodetector; and
    a measuring photodetector that detects emitted luminescence after passing through said collection optics;
    wherein the excitation source is provided in the direct optical path between the sensing material and the measuring photodetector, the optical probe being adapted for handheld use.

2. The optical probe of claim 1, further comprising a transparent sensor substrate coupled between said detachable component and said waveguide configured to allow a sensing material to be deposited.

3. The optical probe of claim 1, wherein said sensing material is deposited directly on said waveguide.

4. The optical probe of claim 1, further comprising an airway adapter operatively coupled to said optical probe to analyze the breath of a user.

5. The optical probe of claim 1, wherein said at least one specified analyte is oxygen, carbon dioxide, pH, phosphate, nitrate, ammonia, chloride or a range of biomolecules such as DNA, enzymes or antibodies.

6. The optical probe of claim 1, further comprising a reference photodiode configured to measure backscatter from said excitation source.

7. The optical probe of claim 1, further comprising at least one sealing ring to provide connection between said outer housing, said waveguide mount, said waveguide, and said detachable component.

8. The optical probe of claim 1, wherein said measuring photo-detector is a measuring photomultiplier tube.

9. An optical probe for detecting luminescence emitted by a sample comprising:
 a parabolic optical waveguide;
 an outer housing configured to hold said optical waveguide having a detachable component;
 a sensing material for detection of at least one analyte;
 an excitation source comprising an LED configured to provide light;
 a half-ball focusing lens configured to focus the light provided by the excitation source onto said sensing material to excite said sensing material; and
 a measuring photodetector that detects emitted luminescence,
 wherein the excitation source is provided in the direct optical path between the sensing material and the measuring photodector, and the parabolic optical waveguide operably directs light from the emitted luminescence past the excitation source onto the photodetector behind the excitation source, the optical probe being adapted for handheld use.

10. An optical probe for detecting luminescence emitted by a sample comprising:
 a parabolic optical waveguide;
 an outer housing configured to hold said optical waveguide having a detachable component;
 a sensing material for detection of at least one analyte;
 an excitation source comprising an LED configured to generate light which is focused by a half-ball lens onto said sensing material to excite said sensing material;
 a measuring photodetector that detects emitted luminescence; and
 an airway adapter operatively coupled to said optical probe to analyze the breath of a user,
 wherein the airway adaptor is provided at the opposite end of the housing to the photodetector, and the excitation source is provided in the direct optical path between the sensing material and the measuring photodetector, the optical probe being adapted for handheld use.

11. The probe of claim 9 including collection optics provided between the photodetector and the excitation source for directing luminescence from the sensing material onto the photodetector.

\* \* \* \* \*